United States Patent [19]

Vincent et al.

[11] 4,048,313

[45] Sept. 13, 1977

[54] BENZENE SULPHONAMIDES PROCESSES FOR PRODUCING THE SAME AND PHARMACEUTICAL COMPOSITIONS INCORPORATING THEM

[75] Inventors: Michel Vincent, Bagneux; Georges Remond, Versailles; Xavier Pascaud, Paris; Jean-Claude Poignant, Bures, Yvette, all of France

[73] Assignee: Science Union et Cie, Neuilly, France

[21] Appl. No.: 540,032

[22] Filed: Jan. 9, 1975

[30] Foreign Application Priority Data

Jan. 9, 1974 United Kingdom .................. 959/74

[51] Int. Cl.$^2$ .................. A61K 31/535; C07D 295/00
[52] U.S. Cl. .............................. 424/248.5; 260/243.3; 544/121; 544/85; 544/60; 544/137; 544/130; 544/141; 544/159

[58] Field of Search ................ 260/247.1 M; 424/248, 424/248.5

[56] References Cited

U.S. PATENT DOCUMENTS 3,896,124 7/1975 Mylari .......................... 260/247.1 M Primary Examiner—Frederick E. Waddell
Attorney, Agent, or Firm—Behr & Woodbridge

[57] ABSTRACT

This application relates to benzenesulphonamides and more specifically to 1-acylamino 2- alcoxy or alcenyloxy 5-morpholinylsulfonyl benzenes and their salts with a mineral or organic acid. It also relates to processes for producing these compounds.

The disclosed compounds are useful for stimulating gastric evacuation while inhibiting emisis and gastric secretion in warm-blooded animals.

11 Claims, No Drawings

BENZENE SULPHONAMIDES PROCESSES FOR PRODUCING THE SAME AND PHARMACEUTICAL COMPOSITIONS INCORPORATING THEM

DESCRIPTION OF THE PRIOR ART

The relevant prior art may be represented with the French Pat. No. 2,167,798 to Sogeras which discloses and claims a specific compound i.e., 2'-methoxy 5'-sulfamoyl 2[(1-ethyl) pyrrolidinyl)] acetanilide. This compound is endowed with anti-emetic properties.

SUMMARY OF THE INVENTION

This invention relates to novel benzene sulphonamides and to processes for producing the same.

More specifically this invention provides the compounds of formula I

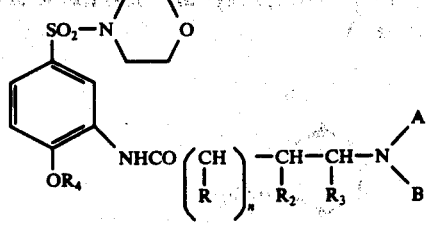

(I)

in which

A and B, which may be identical or different, each represents a lower alkyl group or, together with the nitrogen atom to which they are bonded form a saturated nitrogen-containing heterocycle which may contain another hetero-atom and which has from 3 to 8 ring members, $n$ is zero or an integer from 1 to 3, R represents a hydrogen atom or a lower alkyl group, $R_2$ represents a hydrogen atom or a lower alkyl group, or, together with A, forms an alkylene chain having from 2 to 4 carbon atoms, in which case B is a lower alkyl group and $R_3$ is a hydrogen atom or a lower alkyl group, $R_3$ represents a hydrogen atom or a lower alkyl group or, together with A, forms an alkylene chain which may contain another hetero-atom and which has from 3 to 7 chain members, and, $R_4$ represents a lower alkyl group or a lower alkenyl group. The salts thereof with a mineral or organic acid and their optically-active isomers.

Amongst the compounds of formula I they may be particularly cited as presently preferred compounds:

— those for which $R_2$ and A together form an alkylene chain, having from 2 to 3 carbon atoms which may be interrupted by an extra hetero-atom.

— those for which $R_3$ and A together form an alkylene chain having from 3 to 6 carbon atoms which may be interrupted by an extra hetero-atom.

— those for which A and B are each a lower alkyl radical having from 1 to 4 carbon atoms.

The compounds of the invention are endowed with activating properties on gastric evacuation and with gastric anti-secretory properties. They are devoided of any anti-emetic properties and they do not manifest neuro-depressive action at a significative degree. They may be used in human or veterinary medicine where the foregoing properties are desirable.

This invention relates to benzene-sulphonamides, and more especially to disubstituted m-aminobenzene-sulphonamides.

The present invention provides m-acylamino-benzene-sulphonamides of the general formula

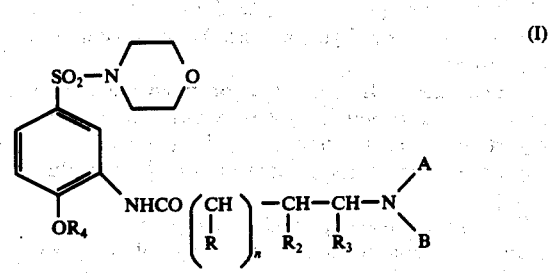

(I)

in which

A and B, which may be identical or different, each represents a lower alkyl group or, together with the nitrogen atom to which they are bonded form a saturated nitrogen-containing heterocycle which may contain another hetero-atom and which has from 3 to 8 ring members, $n$ is zero or an integer from 1 to 3, R represents a hydrogen atom or a lower alkyl group, $R_2$ represents a hydrogen atom or a lower alkyl group, or, together with A, forms an alkylene chain having from 2 to 4 carbon atoms, in which case B is a lower alkyl group and $R_4$ is a hydrogen atom or a lower alkyl group, $R_3$ represents a hydrogen atom or a lower alkyl group or, together with A, forms an alkylene chain which may contain another hetero-atom and which has from 3 to 7 chain members, and, $R_4$ represents a lower alkyl group or a lower alkenyl group.

The term "lower alkyl" is used herein to denote a hydrocarbon group having from 1 to 6 carbon atoms in a straight or branched chain. The term "lower alkenyl" is used herein to denote an ethylenic hydrocarbon chain having from 2 to 6 carbon atoms.

The pairs of substituents A and B or $R_2$ and A or $R_3$ and A can, together with the nitrogen atom to which they are bonded, form a saturated nitrogen-containing heterocycle for example, a piperidine, a pyrrolidine, a hexamethyleneimine or a hexahydroazocine. They may further include another heteroatom selected from the group consisting of nitrogen, oxygen and sulphur.

Examples of such biheterocyclic structures are oxazolidine, morpholine, thiamorpholine, piperazine and diazepines.

These saturated nitrogen-containing heterocycles may also be substituted by one or more lower alkyl radicals, by a phenyl or by a substituted lower alkyl radical such as a hydroxyethyl radical.

From amongst the compounds of the present invention, there may be mentioned more especially:

1-[(N-methylpiperid-2-yl)-acetylamino]-2-methoxy-5-morpholinylsulphonyl-benzene,
1-[(N,N-diethylamino-propionylamino]-2-methoxy-5-morpholinylsulphonyl-benzene and
1-[(N-ethylpiperid-3-yl)-carboxamido]-2-methoxy-5-morpholinylsulphonyl-benzene.

The compounds of the present application exhibit valuable pharmacological properties. More especially, they exhibit gastric anti-secretory properties and have a favourable action on the gastric evacuation which make them useful in human and animal therapy. They differentiate themselves from related compounds from the literature by the absence of any anti-emetic property. Moreover they possess a slight depressive action on the Central Nervous System, and have muscle relaxant properties.

The compounds of the present invention can be used in gastroenterology for the prevention or treatment of digestive disorders connected with psychosomatic disturbances, gastric hyper secretion and gastroduodenal ulcer.

The invention also provides pharmaceutical compositions which contain, as the active ingredient, at least one compound of the general formula I or a therapeutically compatible salt thereof, in admixture or conjunction with an inert pharmaceutical excipient.

For oral, parenteral, rectal or perlingual administration, the pharmaceutical compositions of the present invention can be in the form of uncoated or coated tablets, drinkable or injectable suspensions or solutions packaged in ampoules, multi-dose flasks or self-injectable syringes, suppositories, sublingual tablets, or solutions.

The posology may vary depending on the age of the subject, the therapeutic indication and the method of administration. It ranges from 10 to 100mg per unit dosage and from 20 to 400mg per day, in the man.

The present invention also provides a process for the preparation of the compounds of the general formula I, which comprises condensing a m-amino-benzene-sulphonamide of the general formula

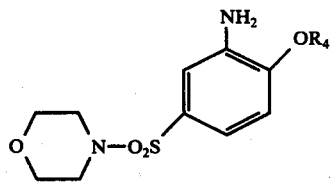 (II)

in which $R_4$ has the meanings specified above, with an aminoalkylcarboxylic acid of the general formula

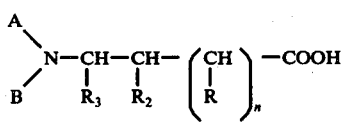 (III)

in which $n$, A, B, R, $R_2$ and $R_3$ have the meanings specified above, or a functional derivative thereof, to produce a corresponding anilide of the general formula I, which, where appropriate, can be salified by addition of an inorganic or organic acid, or can be resolved into its optical isomers when the aminoalkyl-carboxylic acid portion contains at least one asymmetric carbon atom.

It is also possible to use an aminoalkyl-carboxylic acid of the general formula III which is optically active and which has been previously resolved. The anilide produced by condensation is then already resolved.

Functional derivatives of the acids of the general formula III which can be used in the process of the present invention are, for example, the halides such as the acid chloride or bromide, esters such as an alkyl ester of low molecular weight or a phenyl or nitrophenyl ester, or an anhydride or a mixed anhydride produced in situ by reaction with a dicycloalkyl- or a dialkyl-carbodiimide, with ethoxyacetylene, with an alkyl haloformate or with cyanogen bromide.

The acid chloride is preferably used, in the presence of a hydracid acceptor for example, pyridine, triethylamine, 4-dimethylaminopyridine or collidine.

The invention provides also a process for preparing the m aminobenzene-sulphonamides of the general formula II

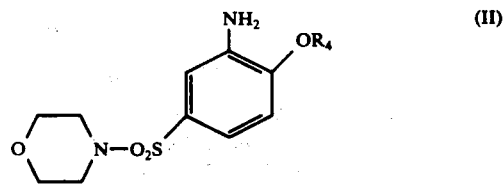 (II)

in which $R_4$ is defined as previously given which consists in condensing a nitrophenylsulphonyl halide of the general formula IV

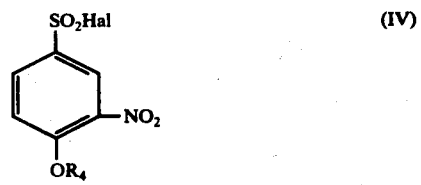 (IV)

in which $R_4$ has the above-given meanings and Hal is a fluorine, chlorine or bromine atom with morpholine, in order to produce a morpholinylsulphonyl derivative of the general formula V

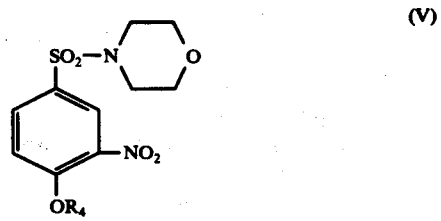 (V)

wherein $R_4$ has the above-given meanings reducing the latter by known methods to produce the corresponding amino derivative of the general formula II

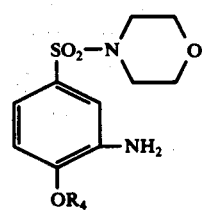

wherein $R_4$ has the above-given meanings.

The compounds of general formula I may also be obtained according to a process which consists in submitting a nitrophenylsulphonyl halide of the general formula IV to the action of diethanolamine in order to produce a bis hydroxyethylsulphonamide of the formula VI

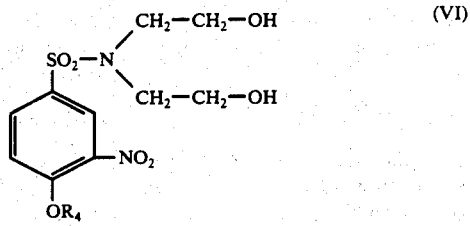

—wherein $R_4$ has the above-given meanings — reducing the latter into the corresponding amino derivative of the formula VII

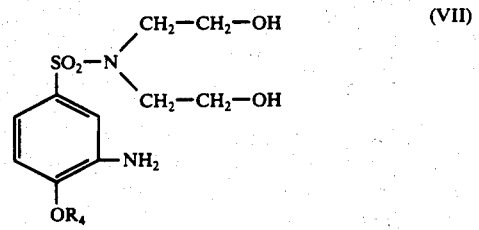

—wherein $R_4$ has the above-given meanings — condensing the amino derivative with an aminocarboxylic acid of the general formula III

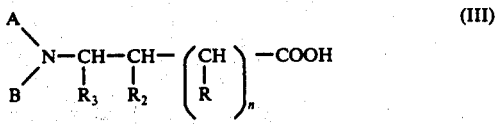

or a functional derivative thereof and finally dehydrating the thus obtained bis hydroxyethylsulphonamide of formula VIII

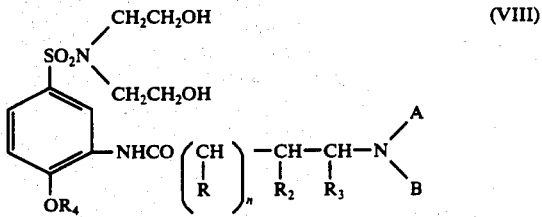

to produce a morpholinylsulphonyl derivative of general formula I.

Preferably the reduction of compounds of general formula V as well as reduction of compounds of general formula VI is performed either using hydrogen in the presence of a catalyst such as platinum or platinum oxyde either using a mixed alkali metal hydride in the presence of aluminium chloride or a palladium salt or a metal in acidic medium.

The dehydration of the bis hydroxyethyl derivative of formula VIII into a compound of general formula I is performed according to known methods such as described by Hampton J. of Am. Chem. Soc. 58, 2338 (1936).

The starting material of general formula IV are known from the literature, more particularly according to the method described by Steinkopf J. Prakt, Chem. 117 (1927) 1-82.

Aminoalkyl carboxylic acids and their functional derivatives have been previously described in the literature. In particular, when they are cyclic, they are produced by catalytic hydrogenation of the corresponding heteroatomic arylcarboxylic acid followed by alkylation at the nitrogen atom.

The following examples are intended to illustrate the invention. They do not limit it in any manner.

PREPARATION OF THE STARTING MATERIAL

Stage A

2-Methoxy-5-morpholinylsulphonyl-nitrobenzene 2,52 g of 2-nitroanisole-4-sulphonyl chloride are dissolved in 25 cm$^3$ of triethylamine. 1ml of morpholine is added and the reaction mixture is heated at about 60° for 2 hours. The mixture is then allowed to return to room temperature and is diluted with 50 ml of water, whilst stirring. Stirring is continued for one hour. The morpholide precipitate is filtered off, drained, and washed with water, then with dilute hydrochloric acid until the wash water is neutral, and finally with more water. The crude 2-methoxy-5-morpholinylsulphonyl-nitrobenzene is recrystallized from ethanol by heating and cooling. The yellow crystals obtained are filtered off, rinsed with cold alcohol and dried. They are used directly for the following stage of the synthesis.

Starting from 2-nitrophenetol 4-sulphonyl chloride and morpholine 2-ethoxy 5-morpholinylsulphonyl nitrobenzene is similarly obtained.

Starting from 2-nitro 1-allyloxy phenyl 4-sulphonyl chloride and morpholine 2-allyloxy 5-morpholinylsulphonyl nitrobenzene is similarly obtained.

Stage B

2-Methoxy-5-morpholinylsulphonyl-aniline 2 g of 2-methoxy-5-morpholinylsulphonyl-nitro-benzene and 0,5 g of iron filings are suspended in 50 ml of water and 0,5 ml of hydrochloric acid is added. The stirred mixture is kept at about 10° by means of a water bath. After the evolution of gas has ceased, the excess iron is filtered off. The acid solution is carefully neutralised by adding sodium carbonate and is then extracted three times with isopropyl ether. The ether phases are combined, washed with water, dried over sodium sulphate, filtered and then evaporated to dryness.

The dry residue of 2-methoxy-5-morpholinylsulphonyl aniline is dissolved in 10 ml of methanol and then petroleum ether is added until crystallisation begins. The mixture is left to stand overnight in a refrigerator and then the crystals are filtered off, drained and dried in vacuo.

1.76 g of 2-methoxy-5-morpholinylsulphonyl-aniline are thus obtained. M.P. = 192°-193°

In the same manner the corresponding 2-ethoxy and 2-allyloxy derivatives are obtained.

EXAMPLE I

1-[(N-Methylpiperid-2-yl)-acetylamino]-5-morpholinylsulphonylmethoxy benzene 1.85 g of ethyl(1-methylpiperid-2-yl)-acetate, 2.70g of 2-methoxy-5-morpholinylsulphonyl-aniline and 0.50 g of a dispersion of sodium hydride in vaseline oil are dissolved in 50 ml of dimethylsulphoxide. The reaction mixture is stirred overnight at room temperature and is then poured into a mixture of ice and water. The crystalline precipitate obtained is filtered off, washed with water and then drained, rinsed with a few ml of pentane and dried in vacuo.

3.39 g of 1-[(N-methylpiperid-2-yl)-acetylamino]-2-methoxy-5-morpholinylsulphonyl-benzene are thus obtained and are recrystallised from benzene for analysis purposes.

The final yield is 3.09g, corresponding to 85% of the theoretical yield. Ethyl(1-methylpiperid-2-yl)-acetate is produced in accordance with the process described by Sperber and col. J. Am. Chem. Soc., 81, 704 (1959).

The corresponding 2-ethoxy and 2-allyloxy analogs are obtained starting from the corresponding 2-ethoxy and 2-allyloxy anilines.

EXAMPLE II

1-(3-Diethylamino-propionylamino)-2-methoxy-5-morpholinylsulphonyl-benzene

In a three-neck flask they are introduced 7.2g 3-diethylaminopropionic acid (hydrochloride) and 180 ml hexamethylphosphorotriamide. The suspension is cooled with an ice-bath and then 2,90 ml thionylchloride are added while maintaining the inner temperature between +5° − +10° C. The reaction mixture progressively gives a yellow solution. After 2 hours stirring 10.9 g of 2-methoxy 5-morpholinylsulphonyl aniline are added portionwise and the whole mixture is kept under stirring for 4 hours at room temperature and then let to stand for a night. The dark solution is thereafter diluted with 1 l ethyl ether and it appears a precipitate. After 1 hour standing the precipitate is collected, suction-filtered and washed with acetone. After thoroughly drying the raw product weighing 11.3g is recovered and further recrystallised from acetone.

1-[3'-diethylaminopropionylamino] 2-methoxy 5-morpholinylsulphonyl benzene melts at 184° C.

The same product may also be obtained by the following procedure:

To a solution of 1.82 g of diethylamino-propionic acid hydrochloride in 20 ml of pyridine, there is added 10 ml of benzene and 2.10 g of dicyclohexyl-carbodiimide. The mixture is let to stand for one hour, with stirring, at room temperature.

The precipitate which forms is filtered off and a solution of 1.5 g of 2-methoxy-5-morpholinylsulphonyl-aniline in 20 ml of pyridine is added to the filtrate. The mixture is stirred for 2 hours.

The reaction mixture is then allowed to return to room temperature and is poured into 50 ml of water. The components are let in contact for 1 hour and then the precipitate is filtered off, washed with water until the wash water is neutral, and then dried in vacuo.

2.61 g of 1-(3'-diethylaminopropionylamino)-2-methoxy-5-morpholinylsulfonyl-benzene are thus obtained.

The 2-ethoxy and the 2-allyloxy derivatives may be obtained in similar conditions.

EXAMPLE III

1-[(N-ethylpiperid-3-yl)carboxamido] 2-methoxy 5-morpholinylsulphonyl benzene

Step A

1-[(N-Ethylpiperid-3-yl)-carboxamido]-2-methoxy-5-di-($\beta$-hydroxyethyl)-sulphamoyl-benzene Following the procedure described in stage A of the preparation of the starting material starting from 2.52 g of 2-nitroanisole-4-sulphonyl chloride and 1.60 g of diethanolamine, there is obtained 2-methoxy-5-di-($\beta$-hydroxyethyl)-sulphamoyl-nitrobenzene.

By reducing 2-methoxy-5-di-($\beta$-hydroxyethyl)-sulphamoyl-nitrobenzene in accordance with the procedure described in stage B, there is obtained 2-methoxy-5-di-($\beta$-hydroxyethyl)-sulphamoyl-aniline.

In a three-neck flask 5.8 g of N-ethylpiperidinyl-3 carboxylic acid hydrochloride and 90 ml hexamethylphosphorotriamide are mixed together until a perfect suspension is obtained — 2.2 ml of thionyl chloride are thereafter added and the suspension is stirred until completely converted into a clear solution— 2.9 g of 2-methoxy 5-di-($\beta$-hydroxyethyl) sulphamoyl aniline are added while keeping the temperature of the reaction mixture below +5° C and the stirring is maintained over the night. The reaction mixture is thereafter diluted 500 ml ethyl ether giving rise to a white precipitate. The ethereous phase is decanted and the insoluble matters are suction-filtered. The raw product is suspended in 50 ml 2 N sodium hydroxide and 25 ml ethanol. The mixture is stirred and the product dissolves progressively at room temperature. After complete solution, ethanol is evaporated off, and the aqueous solution is made alkaline by adding sodium carbonate. The oily product which separates is extracted three times with 15 ml chloroform. The chloroformic solutions are united, dried on sodium sulphate and evaporated off.

The residue weighing 6.7 g is substantially constituted of 1-[(N-ethylpiperid-3-yl)carboxamido] 2-methoxy 5di($\beta$-hydroxyethyl) sulphamoyl benzene. The product is used as such for the next step of the synthesis.

Step B

1[(N-ethylpiperid-3-yl)carboxamido] 2-methoxy 5-morpholinylsulphonyl benzene 6.5 g of 1-[(N-ethylpiperid-3-yl)carboxamido] 2-methoxy 5-di($\beta$-hydroxyethyl)sulphamoyl benzene obtained at stage A of Example III are dissolved in 25 ml methyl cellosolve; 1g sodium hydroxide is added and the solution distilled with steam into hydrochloric acid. A yield of 65% of the hydrochloric acid addition salt is obtained. This, when treated over calcium oxide and extracted with ether, gives about 45% of the morpholinylsulphonyl derivative.

The compound of step A may also be obtained according to the following procedure:

2-Methoxy-5-di-($\beta$-hydroxyethyl)-sulphamoyl-aniline is dissolved in 30 ml of benzene and 5 ml of triethylamine. A solution of (1-ethylpiperidin-3-yl)-carbonyl chloride in 20 ml of benzene is added whilst cooling the reaction mixture is below 10° C during addition. The mixture is stirred for 6 hours at room temperature and then for 1 hour at 60°. The mixture is allowed to return to room temperature and then the solvent is distilled off in vacuo, until the residue is dry.

The dry residue is taken up in 20 ml of isopropyl ether, and washed with water, then with dilute hydrochloric acid and again with water. It is dried and the solvent is evaporated until the residue is dry. 1-[(N-Ethylpiperid-3-yl)-carboxamido]-2-methoxy-5-di-($\beta$-hydroxyethyl)-sulphamoyl-benzene is thus obtained and is recrystallised from acetonitrile for analysis purposes.

(1-Ethylpiperidin-3-yl)-carbonyl chloride is prepared from methyl 1-ethylpiperidinyl-carboxylate [described by Sperber, J. Am. Chem. Soc., 81, 704 (1959)] which is hydrolysed in a dilute hydrochloric acid medium to obtain (1-ethylpiperidin-3-yl)-carboxylic acid hydrochloride. The latter is converted to its chloride by the action of thionyl chloride in an ethereal medium.

Using the procedure of step A and starting of 2-ethoxy 5-di(β-hydroxyethyl) sulphamoyl aniline, 2-butoxy 5-di(β-hydroxyethyl) sulphamoyl aniline, 2-isopropoxy 5-di(β-hydroxyethyl) sulphamoyl aniline or 2-allyloxy 5-(β-hydroxyethyl)sulphamoyl aniline they are obtained respectively the corresponding 2-ethoxy anilide, 2-butoxy anilide, 2-isopropoxy or 2-allyloxy anilide which are in turn dehydrated into the 2-ethoxy 2-butoxy, 2-isopropoxy or 2-allyloxy 5-morpholinylsulphonyl 1-(3-diethylaminopropionylamino) benzene.

They may be further salified by adding to an ethanolic solution of these derivatives the stoechiometric amount of hydrochloric acid or sulphuric acid or acetic acid or benzene sulphonic acid and recovering the thus formed salt by distilling off the solvent.

EXAMPLE IV

Pharmacological study of the compounds of general formula I a. Acute Toxicity

The mean lethal dosis has been determined on batches of mice, previously fastened 12 hours before the experiment. It is graphically determined from at least the results with 4 different doses on respectively 10 mice for each batch. The letality is counted during 8 days after the treatment.

The $LD_{50}$ by intraperitoneal way ranges from 250 to 500mg/kg.

b. Effect on Central Nervous System

This search has for object to determine any action on the behaviour of the mice after treatment with a broad range of dosis from pharmacologically-inactive dosis to lethal dosis. The only symptoms appear at high dosis and are evidenced by a decrease of the muscular tone.

c. Search of an Anti-emetic Activity

The anti-emetic activity has been searched on lots of dogs after subcutaneous injection of 100 μg/kg of Apomorphine. The average effective dosis have been determined in comparison with 1-[(N-ethylpyrrolidin-2-yl)acetyl] 2-methoxy 5-sulphamoyl aniline selected as reference product. At a dosis of 1mg/kg where the reference product insures a complete protection against the emetic effect of apomorphine, the compounds of the invention are devoided of any effect.

d. Effect on Gastric Evacuation

The stimulating effect on the gastric evacuation has been determined by the method of Brodie (Fed. Proceed. 25 (1965) 714). In this method the speed by which pellets of Amberlite of regular shape and previously introduced by tubing in the stomach are expelled, is determined on lots of rats after having be fastened for 12 hours.

At a dosis of 1mg/kg per subcutaneous way the compounds increase by more than 50% the speed of gastric evacuation. In similar experimental conditions the reference product has a $ED_{50}$ of 44mg/kg.

e. Effect on Gastric Secretions

The inhibitory effect on gastric secretions has been determined on lots of rats using the method described by H. G. Shay and coll. The gastric secretions are collected 4 hours after ligature of the pylorus and total acidity thereof is determined by means of an Autopipetting system Radiometer (titration by 0.1 N NaOH until pH = 8,45)

The tested dosis administered by intraperitoneal way ranged from 25 to 100mg/kg. The $ED_{50}$ is about 50mg/kg. In similar experimental conditions at a dosis of 30mg/kg the reference product is without effect.

EXAMPLE V

Tablets containing 50 mg of [(N-methylpiperid-2yl-)acetylamino] 2-methoxy-5-morpholinylsulfonyl benzene per unit dosage

| Active ingredient | 500 g |
|---|---|
| Starch | 225 g |
| Ethyl cellulose | 5 g |
| Calcium carbonate | 200 g |
| Magnesium Stearate | 25 g |
| Talc | 25 g |
| Silica | 20 g | for 10,000 tablets weighing about 100mg.

What we claim is:

1. A *m* acylamino benzene sulphonamide of the formula

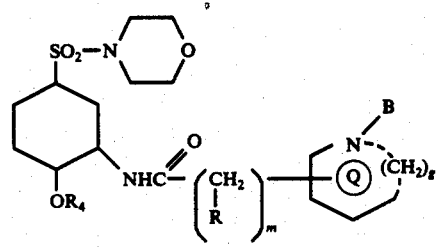

wherein
B is lower alkyl,
m is zero or an integer of 1 to 4, g is zero, 1, or 2, R is a hydrogen atom or a lower alkyl group,
$R_4$ is lower alkyl or lower alkenyl;
wherein the heterocycle designated Q is joined to the $(CH_2)_m$ group at positions 2 or 3 of the said heterocycle.

2. An acid addition salt of the compound of claim 1 with a mineral or organic acid.

3. An optically-active isomer of a compound of claim 1 wherein the aminoacyl side-chain contains at least one asymetric carbon atom.

4. A *m* acylamino benzene sulphonamide of the formula

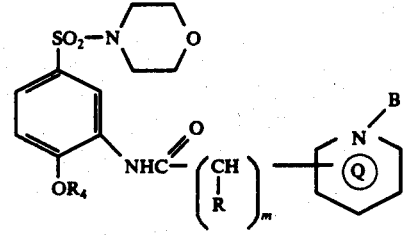

wherein
B is lower alkyl,
m is zero or an integer of 1 to 4,
R is a hydrogen atom or a lower alkyl group,
$R_4$ is lower alkyl or lower alkenyl;
wherein Q is piperidyl joined to the

group at position 2 or 3.

5. A compound according to claim 4 which is 1[(N-ethylpiperid-3yl)carboxamido] 2-methoxy 5-morpholinylsulphonyl benzene.

6. A compound according to claim 4 which is 1-[(N-methylpiperid-2yl)acetylamino] 2-methoxy 5-morpholinylsulphonyl benzene.

7. A pharmaceutical composition for stimulating gastric evacuation while inhibiting emesis and gastric secretion in warm blooded animals suffering from digestive ailments which are in need of the foregoing stimulation of gastric evacuation, including as active ingredient an effective amount of at least one compound of claim 1 or salt thereof with a mineral organic acid in admixture with an inert nontoxic pharmaceutical carrier.

8. A pharmaceutical composition according to claim 7 in which the pharmaceutical carrier is adapted for oral, parenteral, sublingual or rectal administration.

9. A pharmaceutical composition according to claim 7 in the form of tablets, ampuls, multidosage flasks, auto-injectable syringes, suppositories or sublingual tablets.

10. A method for stimulating gastric evacuation while inhibiting emesis and gastric secretions in warm-blooded animals suffering from digestive ailments which are in need of the foregoing stimulation of gastric evacuation which consists in administering to said patients a safe but effective amount of a compound of claim 1 or salt thereof.

11. A method according to claim 10 wherein the safe but effective amount ranges from 0.3 mg/kg to 6.6 mg/kg daily.

* * * * *